US00PP26905P2

(12) United States Plant Patent
Korlipara

(10) Patent No.: US PP26,905 P2
(45) Date of Patent: Jul. 5, 2016

(54) ***LEUCANTHEMUM* PLANT NAMED 'MACAROON'**

(50) Latin Name: *Leucanthemum×superbum*
Varietal Denomination: Macaroon

(71) Applicant: Terra Nova Nurseries, Inc., Canby, OR (US)

(72) Inventor: Harini Korlipara, Canby, OR (US)

(73) Assignee: TERRA NOVA NURSERIES, INC., Canby, OR (US)

( * ) Notice: Subject to any disclaimer, the term of this patent is extended or adjusted under 35 U.S.C. 154(b) by 9 days.

(21) Appl. No.: 14/544,790

(22) Filed: Feb. 18, 2015

(51) Int. Cl.
*A01H 5/02* (2006.01)

(52) U.S. Cl.
USPC ..... Plt./285

(58) Field of Classification Search
USPC ..... Plt./285
CPC ..... A01H 5/025
See application file for complete search history.

*Primary Examiner* — Kent L Bell
(74) *Attorney, Agent, or Firm* — Klarquist Sparkman, LLP

(57) ABSTRACT

A new and distinct *Leucanthemum* plant named 'Macaroon' characterized by double daisy type inflorescences, yellow flower buds and young ray florets, fully open flowers display numerous white ray florets around a large gold disc, excellent bloom size, a low, compact habit, and excellent vigor.

2 Drawing Sheets

Botanical denomination: *Leucanthemum×superbum.*
Variety designation: 'Macaroon'.

BACKGROUND OF THE INVENTION

The present invention relates to a new and distinct cultivar of *Leucanthemum* and given the cultivar name 'Macaroon'. *Leucanthemum* is in the family Asteraceae. This new cultivar originated from a controlled cross between unnamed, proprietary *Leucanthemum×superbum* seedlings. The seed of many crosses was massed so the exact parents are unknown.

Compared to *Leucanthemum* 'Bridal Bouquet', U.S. Plant Pat. No. 24,260, the new cultivar is more double.

Compared to *Leucanthemum* 'Victorian Secret', U.S. Plant Pat. No. 22,654, the new cultivar has a much shorter habit and yellow flower buds and young ray florets rather than white.

SUMMARY OF THE INVENTION

This new *Leucanthemum* cultivar is distinguished as unique with its:

1. double daisy type inflorescences,
2. yellow flower buds and young ray florets,
3. fully open flowers display numerous white ray florets around a large gold disc,
4. excellent bloom size,
5. a low, compact habit, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 2 shows the same plant in bud in early June.

FIG. 3 shows the same plant in late June.

DETAILED PLANT DESCRIPTION

Figure 1:
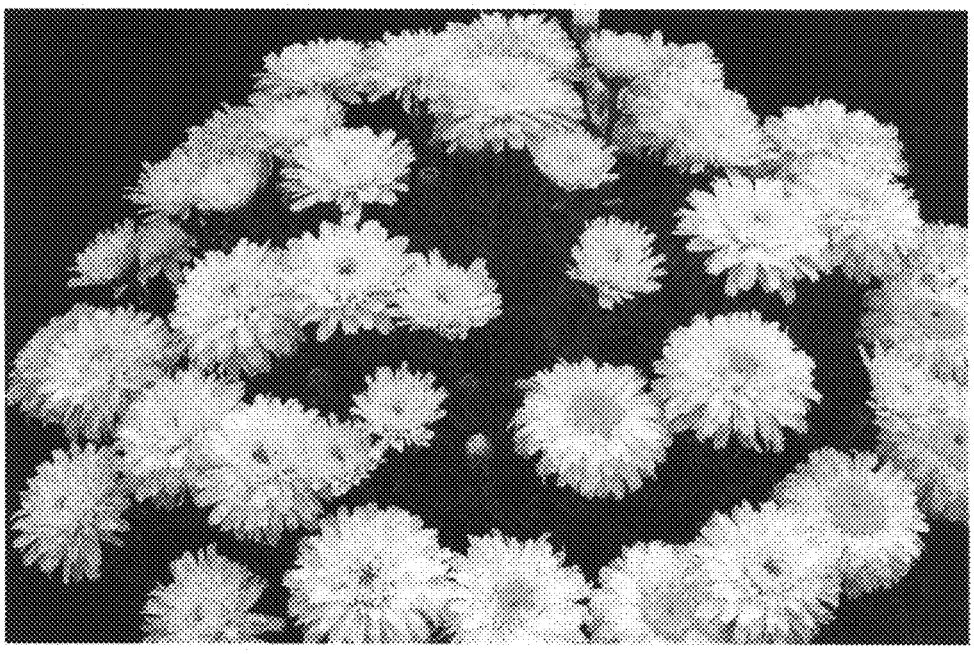
FIG. 1 shows a 2 year old plant growing in the ground in full sun in the trial field (in front of a black background) in mid-June in Canby, Oreg.

The following is a detailed description of the new *Leucanthemum* cultivar based on observations of 1-and-a-half-year-old specimens growing in the field in full sun under typical outdoor conditions in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart,* 5$^{th}$ edition, 2007.

Plant:

*Type.*—Herbaceous perennial.
*Hardiness.*—USDA Zones 5 to 9.
*Size.*—63 cm wide and 35 cm tall to top of inflorescences.
*Form.*—Basal clump.
*# crowns.*—60.
*Vigor.*—Excellent.

Stem (flowering):

*Type.*—Ascending strongly upright with thick, strong stems.
*Number of stems.*—About 55 stems from the crown, each flowering with 1 to 5 inflorescences per stem.
*Size.*—Grows to about 34 cm tall to a terminal inflorescence and 8 mm wide at base.
*Internode length.*—1 cm to 2 cm.

*Surface texture*.—Pubescent.
*Color*.—Green 137A.

Leaves:
*Type*.—Simple.
*Shape*.—Lanceolate.
*Arrangement*.—Alternate.
*Blade size*.—Grows to 10 cm long and 27 mm wide.
*Margins*.—Coarsely serrate.
*Apex*.—Acute.
*Base*.—Clasping.
*Surface texture*.—Pubescent on both sides.
*Venation*.—Pinnate.
*Petiole*.—Sessile.
*Color*.—Topside Green N137A with main vein Yellow Green 147C, bottom side Yellow Green 147B with main vein Yellow Green 147C.

Inflorescence:
*Type*.—Composite on terminal stalked heads.
*Number of inflorescences per plant*.—About 65.
*Size*.—Grows to 8.5 cm wide and 4 cm deep.
*Form*.—Ray florets held upright when young, lower ray florets reflex down with maturity, mature disc is mostly flat.
*Bud* (*immature inflorescence*).—2 cm wide and 2 cm deep, ray florets held vertically and cupped inwards, Yellow 7A.
*Ray florets*.—With 1 pistil and no stamen, about 280 in number (about 25 smaller size near the disc florets), oblong, tip retuse and 2 to 3 lobed, margins entire, base attenuate, average size 4 cm long and 9 mm wide, glabrous on both sides; limb 3 cm long, top and bottom side Yellow 8D with tips 7A when young changing to White NN155B; claw 5 mm long and 2 mm wide, Yellow Green 144B; pistil 6 mm long, ovary 3 mm long, Yellow Green 145D, style 3 mm long, Yellow Green 145D, 2 branched stigma 0.5 mm long, Yellow 13A.
*Disc*.—Slightly concave becoming flat, becoming 10 mm deep and 30 mm wide with maturity, Yellow Orange 17B.
*Disc florets*.—About 450 in number, each 9 mm long and 1.5 mm wide; corolla tubular campanulate, 5.5 mm long and 1.5 mm wide, 5 lobed, glabrous, Yellow 13A on top half and Yellow Green 145A on the bottom half; pistil 1, 8 mm long, ovary 3.5 mm long and Yellow Green 145D, style 5 mm long, Greyed Yellow 160B, 2 branched stigma 0.5 mm long, Greyed Yellow 160B; stamen 5 in number, 5 mm long, filaments 2 mm long, Yellow Green 150D, anthers 3 mm Yellow Orange 17A, pollen Yellow Orange 21A.
*Involucral bracts*.—About 50 in number, in 3 imbricate whorls, area 3.3 cm wide and 10 mm deep, lobes lanceolate to ovate in shape, grow to 9 mm long and 6 mm wide, Green 137A, margin thin and somewhat transparent, Greyed Purple 187A, tip acute, glabrous.
*Receptacle*.—Grows to 21 mm wide and 5 mm deep, Yellow Green 145C.
*Bloom period*.—June through July in Canby, Oreg.
*Fragrance*.—Slight to none.
*Lastingness*.—Each inflorescence lasts about three weeks in Canby, Oreg.

Seeds: None seen.
*Fertility*.—Low.

Disease and pests: The new cultivar is typical to the genus. No known resistances to pests or diseases. No problems have been found in Canby, Oreg.

I claim:

1. A new and distinct *Leucanthemum* plant as herein illustrated and described.

* * * * *

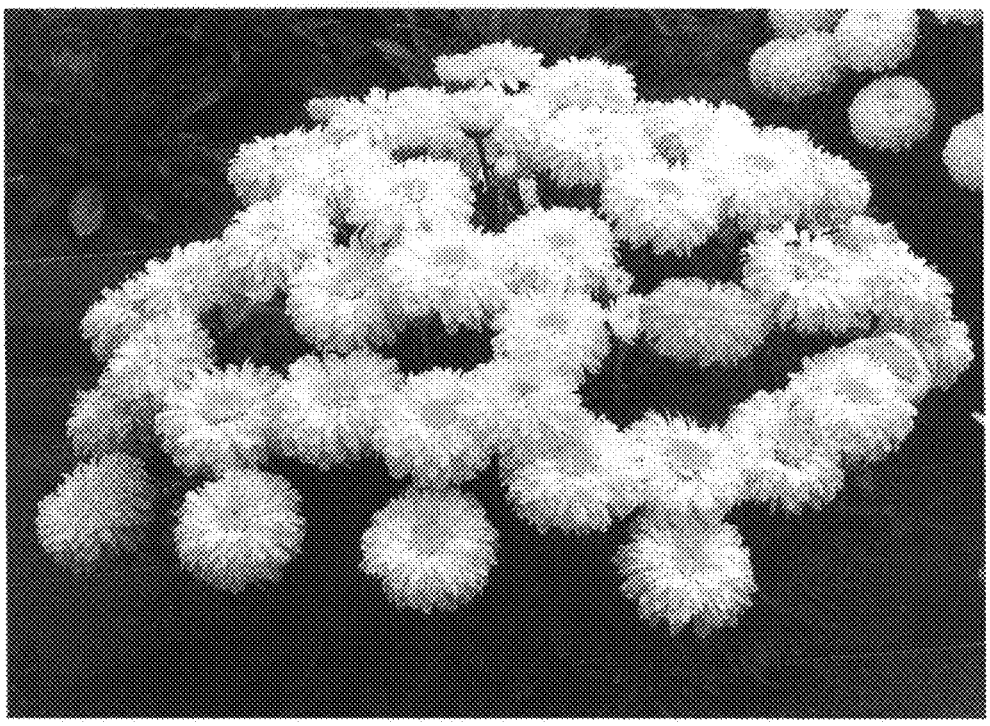

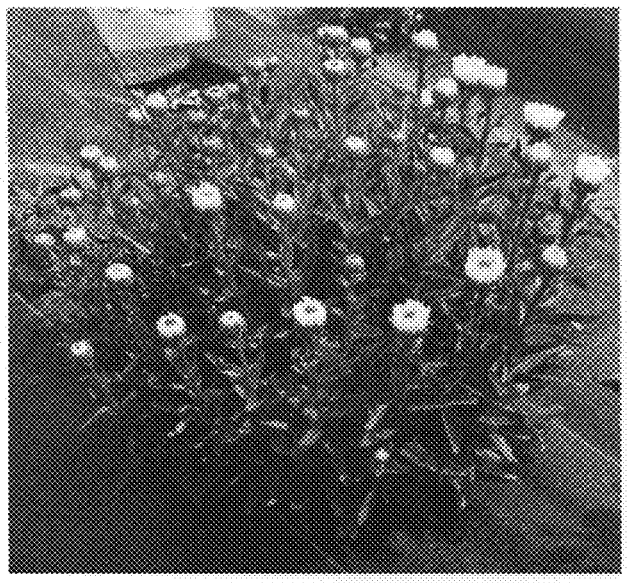
FIG. 2 on left,
FIG 3 below